United States Patent
Sauer

(10) Patent No.: US 9,795,788 B2
(45) Date of Patent: Oct. 24, 2017

(54) IMPLANTABLE MEDICAL DEVICES, AND METHODS OF USE THEREWITH, THAT USE A SAME COIL FOR RECEIVING BOTH COMMUNICATION AND POWER SIGNALS

(71) Applicant: Pacesetter, Inc., Sunnyvale, CA (US)

(72) Inventor: Christian Sauer, Cupertino, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 844 days.

(21) Appl. No.: 13/905,823

(22) Filed: May 30, 2013

(65) Prior Publication Data

US 2014/0358195 A1 Dec. 4, 2014

(51) Int. Cl.
| A61N 1/00 | (2006.01) |
| --- | --- |
| A61N 1/36 | (2006.01) |
| A61N 1/378 | (2006.01) |
| A61N 1/362 | (2006.01) |
| A61N 1/372 | (2006.01) |

(52) U.S. Cl.
CPC ....... *A61N 1/36125* (2013.01); *A61N 1/3787* (2013.01); *A61N 1/37223* (2013.01); *A61N 1/362* (2013.01); *A61N 1/37252* (2013.01)

(58) Field of Classification Search
CPC .................. A61N 1/36125; A61N 1/37223
USPC .......................................................... 607/60
See application file for complete search history.

(56) References Cited

U.S. PATENT DOCUMENTS

| 5,713,939 | A | 2/1998 | Nedungadi | |
| --- | --- | --- | --- | --- |
| 5,733,313 | A | 3/1998 | Barreras, Sr. | |
| 6,577,900 | B1 | 6/2003 | Silvian | |
| 6,631,296 | B1* | 10/2003 | Parramon | A61N 1/08 607/60 |
| 6,772,011 | B2 | 8/2004 | Dolgin | |
| 6,856,838 | B2 | 2/2005 | Parramon | |
| 6,937,894 | B1 | 8/2005 | Isaac | |
| 7,177,698 | B2 | 2/2007 | Klosterman | |
| 2005/0075693 | A1 | 4/2005 | Toy | |
| 2009/0018618 | A1* | 1/2009 | Parramon | A61N 1/37252 607/60 |
| 2009/0024179 | A1* | 1/2009 | Dronov | A61N 1/37223 607/32 |
| 2011/0112610 | A1 | 5/2011 | Rahman | |
| 2011/0112611 | A1 | 5/2011 | Aghassian | |
| 2011/0190852 | A1* | 8/2011 | Dinsmoor | A61B 5/0031 607/60 |

(Continued)

*Primary Examiner* — Nadia A Mahmood
(74) *Attorney, Agent, or Firm* — Theresa A. Raymer

(57) ABSTRACT

Implantable medical devices (IMDs), and methods for use therewith, use a same coil for receiving communication and power signals. An IMD, which is configured to operate in a charge or power mode and in a communication mode, includes a coil, power circuitry and communication circuitry. The coil includes first and second terminals and an intermediate tap therebetween. The power circuitry is coupled, during the charge or power mode, to a first portion of the coil extending between the first and second terminals of the coil. The communication circuitry is coupled to a second portion of the coil extending between the first terminal and the intermediate tap of the coil. A third portion of the coil, extending between the intermediate tap and the second terminal of the coil, is decoupled from the power circuitry during the communication mode, which prevents current from flowing through the third portion of the coil.

14 Claims, 5 Drawing Sheets

(56) References Cited

U.S. PATENT DOCUMENTS

2012/0274270 A1    11/2012   Dinsmoor
2013/0096653 A1     4/2013   Winstrom

* cited by examiner

IMPLANTABLE MEDICAL DEVICES, AND METHODS OF USE THEREWITH, THAT USE A SAME COIL FOR RECEIVING BOTH COMMUNICATION AND POWER SIGNALS

FIELD OF THE INVENTION

Embodiments of the present invention generally pertain to implantable medical devices, and methods for use therewith, that use a same coil for receiving both communication signals and power signals.

BACKGROUND OF THE INVENTION

There are various types of electrically operated implantable medical devices for treating specific diseases and/or physical disorders. For example, one type of electrically operated implantable medical device is a cardiac pacemaker, which can be used, e.g., to restore a sick human heart to a normal rhythm. Another type of electrically operated implantable medical device is a neural stimulator, which can be used, e.g., to stimulate a patient's spinal cord or brain to treat various disorders, including, but not limited to, pain or epileptic seizures. For example, a neural stimulator can be a spinal cord stimulator (SCS) that treats chronic pain by delivering stimulation pulses to a patients spinal cord to induce paresthesia in regions of a patient's body that are afflicted by chronic pain. Other types of implantable neural stimulators include devices that deliver deep brain stimulation, cortical stimulation, cochlear nerve stimulation, peripheral nerve stimulation, vagal nerve stimulation, sacral nerve stimulation, and the like. Other examples of electrically operated implantable medical devices include, but are not limited to, infusion pumps for subcutaneously drug delivery (such as insulin pump), and diagnostic devices for monitoring a patient's condition.

An electrically operated implantable medical device needs a power source. Some electrically operated implantable medical devices are powered by a non-rechargeable battery. When the battery of such a device is depleted, the device must be explanted such that its battery can be replaced or a new device with a new battery can be implanted. Other electrically operated implantable medical devices include rechargeable batteries. The rechargeable battery of such a device can be recharged using a non-implanted device. For example, the implantable device and the non-implanted device can include coils that enable power to be wirelessly transferred, through a patient's skin, from the non-implanted device to the implantable device for the purpose of charging the rechargeable battery. Still other electrically operated implantable medical devices do not include any batteries, but rather, include coils that enable power to be wirelessly transferred, through a patient's skin, from the non-implanted device to the implantable device for the purpose of powering the implantable device. There also exist some electrically operated implantable medical devices that can be directly powered by non-implanted devices, when such a non-implanted device is in range, and can fall back on using their rechargeable battery when the non-implanted device is out of range.

Many electrically operated implantable medical devices are capable of communicating with a non-implanted device, such as a non-implanted programmer. Such electrically operated implantable medical device and non-implanted programmers often include coils that enable communication signals to be wirelessly transferred therebetween through a patient's skin.

Some electrically operated implantable medical devices include a first coil that is used to receive power from a non-implanted device, and a second coil that is used to receive communication signals from a non-implanted device. Other electrically operated implantable medical devices use the same coil for receiving power from a non-implanted device as well as receiving communication signal from a non-implanted device.

SUMMARY OF THE INVENTION

Embodiments of the present invention generally pertain to implantable medical devices (IMDs), and methods for use therewith, that use a same coil for both receiving communication signals as well as for receiving power signals. Such power signals can be used to charge a rechargeable battery of an IMD and/or to produce one or more voltages used to power components of an IMD. Such an IMD can be configured to operate in a first mode and a second mode. The first mode can be a charge mode or a power mode, and the second mode can be a communication mode.

In accordance with specific embodiments, the IMD includes a coil having a first terminal, a second terminal and an intermediate tap between the first and second terminals. The IMD also includes power circuitry and communication circuitry. During the first mode (e.g., the charge or power mode), the power circuitry is coupled to the first and second terminals of the coil. The power circuitry is configured to charge a rechargeable battery and/or power therapy and/or diagnostic circuitry in dependence on a power signal received using the coil from a non-implantable device during the charge or power mode. During the second mode (e.g., the communication mode), the communication circuitry is coupled to the first terminal and the intermediate tap of the coil. The communication circuitry is configured to demodulate communication signals received using the coil from a non-implantable device during the second mode (e.g., the communication mode). Advantageously, the communication circuitry can also be coupled to the first terminal and the intermediate tap of the coil during the charge mode, without damaging the communication circuitry.

In accordance with certain embodiments, a first portion of the coil, which extends between the first and second terminals of the coil, is used for receiving the power signal during the charge or power mode. A second portion of the coil, which extends between the first terminal and the intermediate tap of the coil, is used for receiving the communication signal during the communication mode. The first portion of the coil may include the entire coil. The second portion of the coil includes only some of the first portion of the coil, and thus, has a shorter length than the first portion of the coil.

In accordance with certain embodiments, the power circuitry includes a rectifier coupled, during the charge or power mode, to the first and second terminals of the coil. Such a rectifier is configured to rectify an AC current generated between the first and second terminals of the coil in dependence on the power signal received by the coil from a non-implantable device during the charge or power mode. In accordance with some embodiments, a capacitor is coupled to an output of the rectifier to provide a nearly DC voltage in dependence on a rectified current produced by the rectifier. This nearly DC voltage can be used to produce one or more voltages used to charge a rechargeable battery or be otherwise used to power components of the IMD. In accordance with certain embodiments, the IMD includes a switch between the second terminal of the coil and an input terminal of the rectifier. The switch is used to couple the second terminal of the coil to the input terminal of the rectifier during the charge or power mode. By contrast, during the communication mode, the switch is used to decouple the second terminal of the coil from the input terminal of the rectifier, thereby preventing current from flowing through a portion of the coil between the intermediate tap and the second terminal of the coil during the communication mode. The switch, by decoupling the second terminal of the coil from the input terminal of the rectifier during the communication mode, reduces an inductance of the coil during the communication mode as compared to an inductance of the coil during the charge or power mode. The switch, by decoupling the second terminal of the coil from the input terminal of the rectifier (wherein the rectifier is part of the power circuitry) during the communication mode, also reduces the loading on the coil during the communication mode as compared to the loading on the coil during the charge or power mode. In other words, during the communication mode, the load presented by the power circuitry (which includes the rectifier) to the coil is removed using the switch, leaving only the high impedance loading of the communication circuitry. By reducing the loading on the coil during the communication mode, attenuation of the communication signal (that would otherwise occur if the loading on the coil was not reduced) is avoided.

In accordance with certain embodiments, the IMD also includes first and second coupling capacitors, and the rectifier includes first and second input terminals. During the charge or power mode, the first coupling capacitor is coupled between the first terminal of the coil and the first input terminal of the rectifier, and the second coupling capacitor is coupled between the second terminal of the coil and the second input terminal of the rectifier.

Additionally, the IMD can include a diode coupled between the first terminal of the coil and a ground reference, wherein the diode sets a DC reference point without sourcing or sinking any current. Because the ground reference has no connection to a ground outside of the IMD, this ground reference is relative to the IMD.

Embodiments of the present invention are also related to methods for use by an IMD having a coil and a rechargeable battery, wherein the IMD is configured to operate in a charge mode and a communication mode. In accordance with certain methods, during the charge mode, a first portion of the coil, which may include the entire coil, is used to receive a power signal from a non-implantable device. Additionally, during the charge mode, the rechargeable battery of the IMD is charged in dependence on the power signal received using the first portion of the coil. During the communication mode, a second portion of the coil, which has a shorter length than the first portion of the coil, is used to receive a communication signal from a non-implantable device. Additionally, during the communication mode, the communication signal received using the second portion of the coil is demodulated.

This summary is not intended to be a complete description of the invention. Other features and advantages of the invention will appear from the following description in which the preferred embodiments have been set forth in detail, in conjunction with the accompanying drawings and claims.

DETAILED DESCRIPTION

Figure 1:
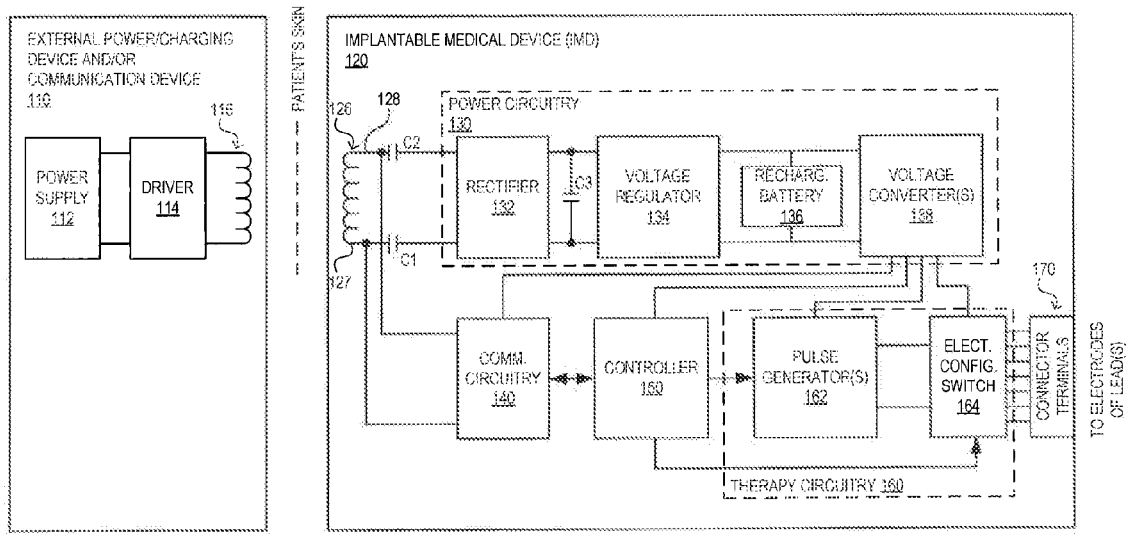
FIG. 1 illustrates an exemplary system including an electrically operated implantable medical device that uses the same coil for receiving power from a non-implanted device as well as receiving communication signals from a non-implanted device.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

Charging of a rechargeable battery of an electrically operated implantable medical device requires a voltage higher than the voltage of the battery to be charged. For example, a 3.8 Volt (V) battery typically needs about 6.5V DC to be charged. Generating that level of DC voltage requires an even larger AC voltage applied to the coil of an implantable device, typically over 14V peak-to-peak.

As mentioned above, some electrically operated implantable medical devices use the same coil for receiving power from a non-implanted device as well as receiving communication signals from a non-implanted device. FIG. 1 illustrates a system that includes an example of such an implantable medical device. More specifically, the system of FIG. 1 includes a non-implanted device 110 (also known as an external device) and an implantable medical device (IMD) 120. The non-implanted device 110 can be used for charging, powering and/or communicating with the IMD 120. Alternatively, a first non-implanted device can be used for charging and/or powering the IMD 120, and a second non-implanted device can be used for communicating with the IMD 120.

The non-implanted device 110 is shown as including a power supply 112, driver circuitry 114 and a coil 116. The power supply 112 can be, for example, a battery or circuitry that converts AC power received from an AC power outlet to DC power. The driver circuitry 114 can be circuitry that drives the coil with an AC signal for the purpose of recharging, powering and/or communicating with an implantable device, such as IMD 120. Accordingly, the driver circuitry 114 can, for example, include a DC-to-AC converter as well as communication circuitry. While not specifically shown, the non-implanted device can also include a controller, which can be part of or separate from the driver circuitry 114. Since embodiments of the present invention primarily relate to an IMD, not a non-implanted device, additional details of the non-implanted device 110 are not provided.

The IMD 120 is shown as including a coil 126, power circuitry 130, communication circuitry 140, a controller 150, therapy circuitry 160 and connector terminals 170. The power circuitry 130 is shown as including a rectifier 132, a voltage regulator 134, a rechargeable battery 136 and voltage converter(s) 138. The rechargeable battery 136 can be, e.g., a lithium ion battery, but is not limited thereto. The IMD 120 is also shown as including coupling capacitors C1 and C2, which can also be referred to as DC blocking capacitors since they are used to block DC signals and pass AC signals. Where the power circuitry 130 is used for charging the rechargeable battery, the power circuitry 130 can alternatively be referred to as charge circuitry.

The IMD 120 is configured to operate in both a charge (or power) mode and a communication mode. The IMD 120 can switch between its modes periodically or based on some other schedule, and/or in response to commands from the non-implanted device 110, but is not limited thereto. When in the charge or power mode, the coil 126 is used for receiving a power signal from the non-implanted device 110. More specifically, the coil 126 of the IMD 120 enables near field coupling with the coil 116 of the non-implanted device 110. When the non-implanted device 110 transmits a power signal by radiating RF power using its coil, an inductive coupling between the coil 116 of the non-implanted device 110 and the coil 126 of the IMD 120 causes current to be induced in the coil 126 of the IMD. This can more generally be referred to as the IMD receiving the power signal. The received power signal, which is an AC signal, is rectified by the rectifier 132 of the power circuitry 130. The output of the rectifier 132, which can be referred to as a rectified signal, is smoothed by a capacitor C3 of the power circuitry 130, to produce a nearly DC voltage signal, albeit one with a large amount of voltage ripple. This nearly DC voltage signal is provided to the voltage regulator 134, which outputs a substantially constant DC voltage signal. This substantially constant DC voltage signal, output by the voltage regulator 134, can be used to recharge the rechargeable battery 136. Additionally (or alternatively, if the IMD 120 does not include the rechargeable battery 136), the substantially constant DC voltage signal output by the voltage regulator 134, can be provided directly to the voltage converter(s) 138. The voltage converter(s) 138 receives a DC voltage from the rechargeable battery 136 (and/or from the voltage regulator 134) and steps-up and/or steps-down this voltage to various voltage levels used for powering the various other components of the IMD 120, including, but not limited to the communication circuitry 140, the controller 150 and the therapy circuitry 160. The IMD 120 can also include further circuitry, such as, but not limited to, diagnostic circuitry and over voltage protection circuitry.

The therapy circuitry 160 is shown as including a pulse generator 162 that is configured to produce stimulation pulses that are used for cardiac stimulation and/or neuro-stimulation. The pulse generator 162 may include dedicated, independent pulse generators, multiplexed pulse generators or shared pulse generators, which is/are controlled by the controller 150 via control signals to trigger or inhibit the stimulation pulses. The therapy circuitry 160 is also shown as including an electrode configuration switch 164. The therapy circuitry 160 can alternatively include an infusion or other type of drug pump for subcutaneously drug delivery (such as an insulin pump).

The controller 150 can control the pulse generator 162 to generate stimulation pulses, and control the electrode configuration switch 164 to couple the stimulation energy to selected electrodes of one or more selected leads. Additionally, the controller 150 can control the electrode configuration switch 164 to select different electrode configurations for delivery of stimulation energy from the pulse generator 162. More specifically, the controller 150 can control the pulse generator 162 and the electrode configuration switch 164 to deliver stimulation energy in accordance with selected cardiac- and/or neuro-stimulation parameters, which can specify a lead, an electrode configuration for the specified lead, and one or more pulse parameters and/or delay parameters. The controller 150 can include one or more of a microprocessor, a microcontroller, a digital signal processor (DSP), an application specific integrated circuit (ASIC), a field-programmable gate array (FPGA), a state machine, or similar discrete and/or integrated logic circuitry. The controller 150 can further include RAM or ROM memory, logic and timing circuitry and I/O circuitry.

The electrode configuration switch 164 can include a switch array, switch matrix, multiplexer, and/or any other type of switching device suitable to selectively couple connector terminals 170 of a connector (also known as a header) to the pulse generator 162 and/or to sense circuitry (not shown in FIG. 1). The distal end(s) of one or more implantable cardiac and/or neural stimulation leads (not specifically shown) can be connected to the connector.

The coil 126 is shown as including a first terminal 127 and a second terminal 128, which may or may not correspond to first and second ends of the coil 126. In the embodiment of FIG. 1, the power circuitry is coupled, by the coupling capacitors C1 and C2, to the first and second terminals 127 and 128 of the coil 126. Additionally, in the embodiment of FIG. 1, the communication circuitry 140 is coupled, upstream of the coupling capacitors C1 and C2, to the same first and second terminals 127 and 128 of the same coil 126. A potential problem with this setup is that the communication circuitry 140 must be able to withstand the relatively high voltages needed to charge the rechargeable battery and/or power the voltage converter(s) 138 (otherwise, the communication circuitry 140 will be damaged), while also maintaining sufficient sensitivity to be able to detect and demodulate communication signals. For example, as mentioned above, a 3.8V battery typically needs about 6.5V DC to be charged, and generating that level of DC voltage typically requires an AC voltage of over 14V peak-to-peak be applied to the coil 126. For various reasons (e.g., power efficiency), it would be beneficial if the communication circuitry 140 were designed for only low voltage (e.g., less than 3.3V) operation. However, if such low voltage operation communication circuitry 140 were connected to the coil 126 as shown in FIG. 1, such communication circuitry 140 would be damaged when the coil 126 received a relatively high voltage power signal from the non-implanted device 110.

Figure 2:
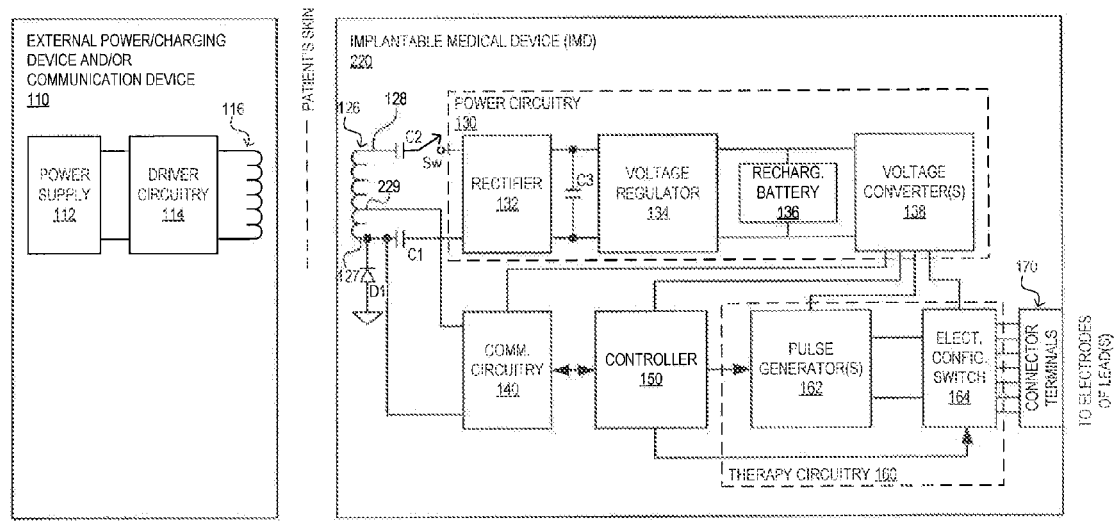
FIG. 2 illustrates a system, according to an embodiment of the present invention, including an electrically operated implantable medical device that uses the same coil for receiving power from a non-implanted device as well as receiving communication signals from a non-implanted device.

Certain embodiments of the present invention, which will now be described with reference to FIG. 2, enable the same coil 126 to be used during both the charge (or power) mode as well as during the communication mode, without requiring that the communication circuitry 140 be able to tolerate high voltages (e.g., greater than 3.3V). Referring to FIG. 2, the IMD 220 is similar to the IMD 120 in that it includes many of the same components, labeled in the same manner, as the IMD 120. Accordingly, such components, which were already discussed above with reference to FIG. 1, need not be described again. One of the differences in FIG. 2 is that the coil 126 of the IMD 220 in FIG. 2 includes an intermediate tap 229 between the first terminal 127 and the second terminal 128 of the coil 126. Another difference in FIG. 2 is that the IMD 220 includes a switch (Sw) that can selectively couple or decouple one of the input terminals of the rectifier 132 to or from the second terminal 128 of the coil. The switch (Sw) can be controlled, e.g., by the controller 150 or the communication circuitry 140, or by some other circuitry. Additionally, in accordance with an embodiment, a diode D1 is coupled between the first terminal 127 of the coil 126 and a ground reference, as shown in FIG. 2, in order to set a DC reference point without sourcing or sinking any current. This ground reference is relative to the IMD 220, because the ground reference has no connection to a ground outside of the IMD 220.

As was the case with the IMD 120, the IMD 220 is configured to operate in both a charge (or power) mode and a communication mode. The IMD 220 can switch between its modes periodically or based on some other schedule, and/or in response to commands from the non-implanted device 110, but is not limited thereto. A first portion of the coil 126, which extends between the first and second terminals 127 and 128 of the coil 126, is used for receiving a power signal during the charge or power mode. By contrast, a second portion of the coil, which extends between the first terminal 127 and the intermediate tap 129 of the coil 126, is used for receiving a communication signal during the communication mode. More generally, a first portion of the coil 126, which may include the entire coil 126, is used for receiving the power signal during the charge or power mode; and a second portion of the coil, which has a shorter length than the first portion of the coil, is used for receiving a communication signal during the communication mode. The power signal can be used to charge the rechargeable battery 136 that is used to produce voltage(s) for use in powering components of the IMD, or to generate voltages (without the use of a rechargeable battery) for use in powering components of the IMD. The communication signal can be used to program the IMD, adjust stimulation parameters of the IMD, download data to the IMD, upload date from the IMD and/or the like.

Figure 3:
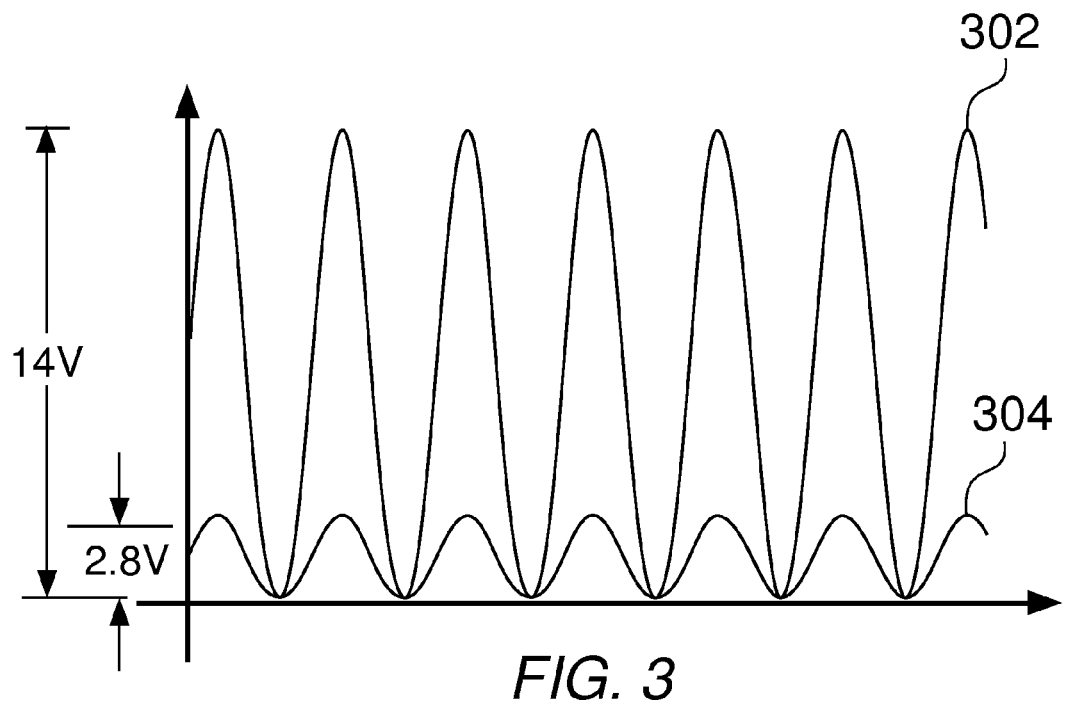
FIG. 3 illustrates how the coil in FIG. 2 can be used to produce different peak-to-peak voltage signals for the power circuitry and the communication circuitry.

The intermediate tap 229 of the coil 126 is used to enable different voltages to be seen by the power circuitry 130 and the communication circuitry 140. In other words, the intermediate tap 229 of the coil 126 is used to present a different peak-to-peak voltage to the communication circuitry 140 than is presented to the power circuitry 130. More specifically, because the communication circuitry 140 is coupled to the portion of the coil 126 between the first terminal 127 and intermediate tap 229 of the coil 126, during the charge or power mode the communication circuitry 140 is only subject to a fraction of a total voltage generated by the coil 126. Even more specifically, the total voltage seen at the intermediate tap 229 is scaled by a ratio of the inductance between second portion of the coil 126 (which extends between the first terminal 127 and the intermediate tap 229 of the coil) and the first portion of the coil 126 (which extends between the first terminal 127 and second terminal 128 of the coil). For example, assuming that a desired charge or power inductance is about 1 millihenry (mH), and that a desired communication inductance is about 220 microhenries (uH), this gives a ratio of about 5 (i.e., 1 mH/220 uH~5). Assuming the power signal received by the coil 126 during the charge or power mode is about 14V peak-to-peak, this would limit the voltage seen by the communication circuitry 140 to about 2.8V peak-to-peak (i.e., 14V/5=2.8V). In other words, the power signal seen by the communication circuitry 140 would be attenuated by a factor of ~5. FIG. 3 illustrates an example 14V peak-to-peak signal 302 seen by the power circuitry 130 and an example 2.8V peak-to-peak signal 304 seen by the communication circuitry 140 during the charge or power mode. In accordance with an embodiment, during the charge or power mode the 2.8V peak-to-peak signal 304 is passed unchanged to the communication circuitry 140 except for the reduction in amplitude, i.e., it is not filtered in any way. In an embodiment, during the charge or power mode the power signal seen by the communication circuitry 140 is ignored by the communication circuitry 140.

The switch (Sw) is used to limit the inductance of the coil 126 when the IMD 220 is in its communication mode. More specifically, when the switch (Sw) is open, the portion of the coil 126 between the intermediate tap 229 and the second terminal 128, which is not connected to the communication circuitry 140, has no current flow in it. This reduces an inductance of the coil 126 during the communication mode as compared to an inductance of the coil 126 during the charge or power mode. The switch (Sw) is also used to avoid attenuation of communication signals received by the coil 126 during the communication mode. The switch (Sw), by decoupling the second terminal 128 of the coil 126 from an input terminal of the rectifier 132 (wherein the rectifier 132 is part of the power circuitry 130) during the communication mode, also reduces the loading on the coil 126 during the communication mode as compared to the loading on the coil 126 during the charge or power mode. In other words, during the communication mode, the load presented by the power circuitry 130 (which includes the rectifier 132) to the coil 126 is removed using the switch (Sw), leaving only the high impedance loading of the communication circuitry 140. By reducing the loading on the coil 126 during the communication mode, attenuation of the communication signal (that would otherwise occur if the loading on the coil 126 by the power circuitry 130 were not removed) is avoided. This will prevent attenuation of any communication signals that may be sent during the communication mode. Without the switch (Sw), the communication signals would be attenuated by the same factor (e.g., ~5) as the power signals.

A benefit of using the same coil during both the charge or power mode as well as the communication mode is that a single coil takes up less space and costs less than two coils. Additionally, if the same non-implanted device 110 is used for both charging (or powering) and communicating with the IMD 220, then an added benefit of using the same coil for both charging (or powering) and communicating with the IMD 220 is that the communication circuitry 140 can easily determine the mode of the IMD 220. This can lead to optimizations in the amount of time that the non-implanted device 110 should be in close proximity with the patient within which the IMD 220 is implanted.

The IMD 220 can be a cardiac stimulation device, such as a pacemaker and/or an implantable cardioverter-defibrillator (ICD). The IMD 220 can alternatively be a neural stimulator, such as a spinal cord stimulator (SCS), or a device that delivers deep brain stimulation, cortical stimulation, cochlear nerve stimulation, peripheral nerve stimulation, vagal nerve stimulation, sacral nerve stimulation, or the like. The IMD 220 can alternatively or additionally be a subcutaneously drug delivery device (such as insulin or other drug pump), or a diagnostic device for monitoring a patient's condition. The IMD 220 can also be a device that delivers various different types stimulation, performs drug delivery and/or performs patient monitoring. In other words, the IMD 220 can perform multiple functions, wherein each of the functions is performed by circuitry that needs to be powered.

Figure 4:
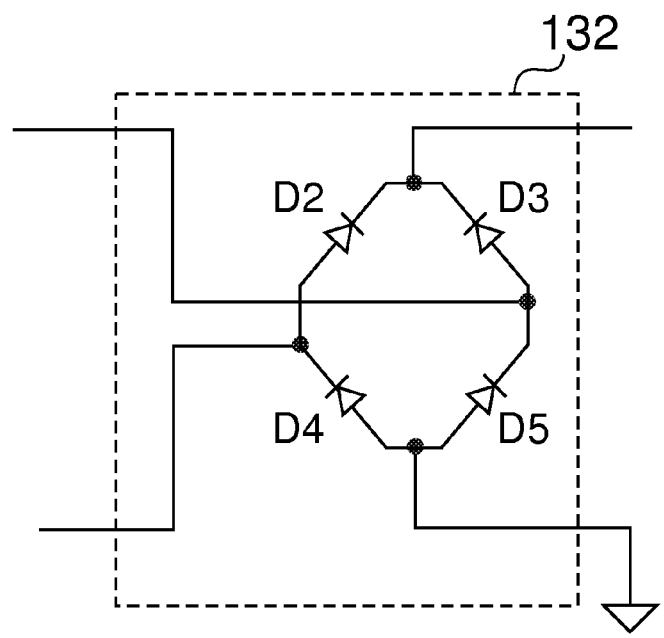
FIG. 4 illustrates an exemplary implementation of the rectifier shown in FIG. 2.

FIG. 4 illustrates exemplary details of the rectifier 132, according to one embodiment. Referring to FIG. 4, the rectifier is 132 is shown as being a standard four diode rectifier, including diodes D2, D3, D4 and D5, configured to provide full-wave rectification. Alternative types rectifiers, such as, but not limited to other types of full-wave rectifiers or less efficient half-wave rectifiers can alternatively be used, and are within the scope of an embodiment of the present invention.

Figure 5:
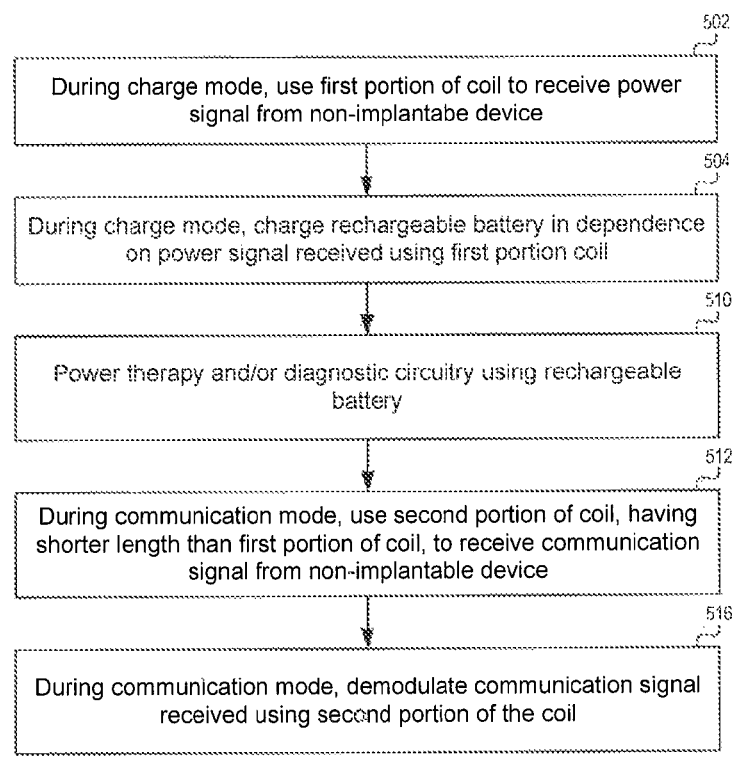
FIGS. 5 and 6 are high level flow diagrams that are used to summarize methods according to various embodiments of the present invention.

FIG. 5 is a high level flow diagram that is used to summarize methods according to various embodiments of the present invention. The methods described with reference to FIG. 5 are for use by an IMD having a coil and a rechargeable battery, wherein the IMD is configured to operate in a charge mode and a communication mode. Referring to FIG. 5, during a charge mode, the method includes using a first portion of the coil, which may include the entire coil, to receive a power signal from a non-implantable device, as indicated at step 502, and charging the rechargeable battery of the IMD in dependence on the power signal received using the first portion of the coil, as indicated at step 504. In accordance with certain embodiments, the method includes rectifying an AC current signal produced by the first portion of the coil in dependence on the received power signal, and using the rectified current signal for charging the rechargeable battery of the IMD at step 504. Using the rectified current signal for charging the rechargeable battery can include, e.g., using circuitry such as the capacitor C3 and the voltage regulator 134 to generate a DC voltage that is used to charge the rechargeable battery. Additionally, the method can include powering therapy circuitry and/or diagnostic circuitry using the rechargeable battery, as indicated at step 510. This can include, but is not limited to, producing, using a voltage produced using the rechargeable battery, stimulation pulses that are used for cardiac stimulation and/or neurostimulation. The therapy circuitry can alternatively, or additionally, include a drug pump that is powered using a voltage produced using the rechargeable battery. The diagnostic circuitry can include one or more sensors or other circuitry that can monitor a condition or metric, such as a patient's glucose concentration or blood pressure.

Still referring to FIG. 5, during the communication mode, the method includes using a second portion of the coil, which has a shorter length than the first portion of the coil, to receive a communication signal from a non-implantable device, as indicated at step 512, and demodulating the communication signal received using the second portion of the coil, as indicated at step 514.

As explained above, the communication signal and the power signal can be received from the same non-implantable device, or from different non-implantable devices. In accordance with certain embodiments, the coil includes a first terminal, a second terminal and an intermediate tap between the first and second terminals. In such embodiments, the first portion of the coil, used during the charge mode at steps 502 and 504, extends between the first and second terminals of the coil; and the second portion of the coil, used during the communication mode at steps 512 and 514, extends between the first terminal of the coil and the intermediate tap of the coil. In accordance with certain embodiments, step 502 includes coupling the second terminal (e.g., 128) of the coil to an input terminal of charging circuitry during the charge mode, and step 512 includes decoupling the second terminal (e.g., 128) of the coil from the input terminal of the charging circuitry during the communication mode, to thereby reduce an inductance of the coil during the communication mode as compared to an inductance of the coil during the charge mode. By decoupling the second terminal of the coil from the input terminal of the charging circuitry during the communication mode, current is prevented from flowing through a third portion of the coil, which extends between the intermediate tap and the second terminal of the coil. In accordance with certain embodiments, the therapy circuitry and/or diagnostic circuitry can be powered at step 510, using the rechargeable battery, during both the charge mode and the communication mode.

Additionally, the method can include setting a DC reference point for the coil without sourcing or sinking any current. This can be accomplished using the diode D1, as described above with reference to FIG. 2.

Figure 6:
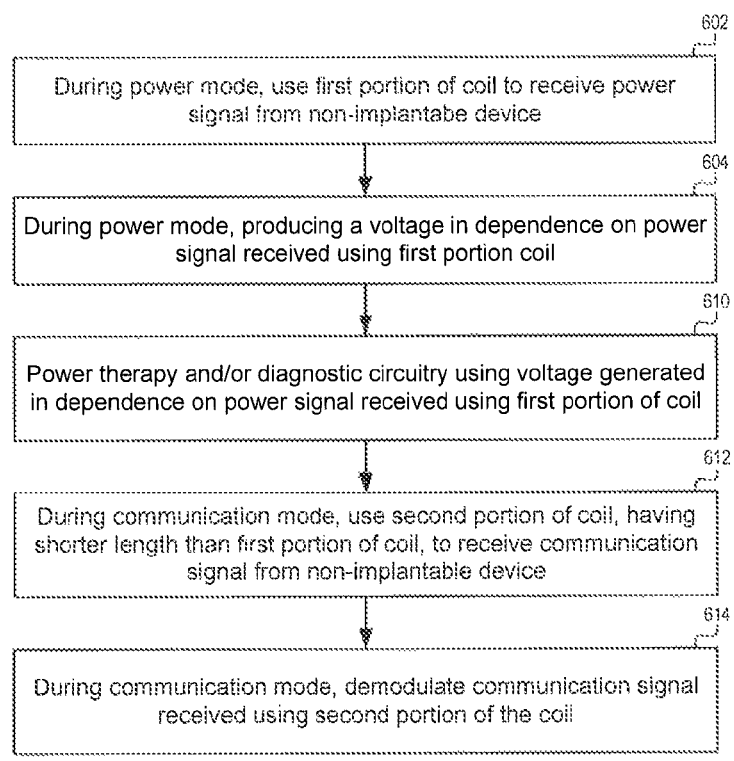

FIG. 6 is a high level flow diagram that is used to summarize methods according to other embodiments of the present invention. The methods described with reference to FIG. 6 are for use by an IMD having a coil, wherein the IMD is configured to operate in a power mode and a communication mode. Referring to FIG. 6, during the power mode, the method includes using a first portion of the coil, which may include the entire coil, to receive a power signal from a non-implantable device, as indicated at step 602, and producing a voltage in dependence on the power signal received using the first portion of the coil, as indicated at step 604. In accordance with certain embodiments, the method includes rectifying an AC current signal produced by the first portion of the coil in dependence on the received power signal, and using the rectified current signal for producing the voltage at step 604. Additionally, the method can include powering therapy circuitry and/or diagnostic circuitry using the voltage generated at step 604, as indicated at step 610. The therapy circuitry can be used to produce stimulation pulses that are used for cardiac stimulation and/or neurostimulation. The therapy circuitry can alternatively, or additionally, include a drug pump that is powered using the voltage generated at step 604. The diagnostic circuitry can include one or more sensors or other circuitry that can monitor a condition or metric, such as a patient's glucose concentration or blood pressure.

Still referring to FIG. 6, during the communication mode, the method includes using a second portion of the coil, which has a shorter length than the first portion of the coil, to receive a communication signal from a non-implantable device, as indicated at step 612, and demodulating the communication signal received using the second portion of the coil, as indicated at step 614.

In accordance with certain embodiments, the coil includes a first terminal, a second terminal and an intermediate tap between the first and second terminals. In such embodiments, the first portion of the coil, used during the power mode at steps 602 and 604, extends between the first and second terminals of the coil; and the second portion of the coil, used during the communication mode at steps 612 and 614, extends between the first terminal of the coil and the intermediate tap of the coil. In accordance with certain embodiments, step 602 includes coupling the second terminal (e.g., 128) of the coil to an input terminal of power circuitry during the power mode, and step 604 includes decoupling the second terminal (e.g., 128) of the coil from the input terminal of the power circuitry during the communication mode, to thereby reduce an inductance of the coil during the communication mode as compared to an inductance of the coil during the power mode. By decoupling second terminal of the coil from the input terminal of the power circuitry during the communication mode, current is prevented from flowing through a third portion of the coil, which extends between the intermediate tap and the second terminal of the coil.

Additionally, the method can include setting a DC reference point for the coil without sourcing or sinking any current. This can be accomplished using the diode D1, as described above with reference to FIG. 2.

Embodiments of the present invention have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 5 and 6. For another example, it is possible to change the boundaries of some of the blocks shown in FIG. 2.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. An implantable medical device (IMD) configured to operate in at least two different modes, the IMD comprising:
   a coil including a first terminal, a second terminal and an intermediate tap between the first and second terminals;
   power circuitry coupled, during a charge or power mode, to the first and second terminals of the coil, and configured to at least one of charge a rechargeable battery or power therapy and/or diagnostic circuitry in dependence on a power signal received using the coil from a non-implantable device during the charge or power mode; and
   communication circuitry coupled, during a communication mode, to the first terminal and the intermediate tap of the coil, and configured to demodulate a communication signal received using the coil from a non-implantable device during the communication mode;
   wherein a first portion of the coil, which extends between the first and second terminals of the coil, is used for receiving the power signal during the charge or power mode;
   wherein a second portion of the coil, which extends between the first terminal and the intermediate tap of the coil, is used for receiving the communication signal during the communication mode;
   wherein the power circuitry includes a rectifier coupled, during the charge or power mode to the first and second terminals of the coil;
   further comprising a switch between the second terminal of the coil and an input terminal of the rectifier;
   wherein the switch is configured to couple the second terminal of the coil to the input terminal of the rectifier during the charge or power mode;
   wherein the switch is configured to decouple the second terminal of the coil from the input terminal of the rectifier during the communication mode, thereby preventing current from flowing through a third portion of the coil, which extends between the intermediate tap and the second terminal of the coil, during the communication mode; and
   wherein the switch, by decoupling the second terminal of the coil from the input terminal of the rectifier during the communication mode, reduces an inductance of the coil during the communication mode as compared to an inductance of the coil during the charge or power mode.

2. The IMD of claim 1, wherein:
   the first portion of the coil which is used for receiving the power signal during the charge or power mode, includes the entire coil; and
   the second portion of the coil, which is used for receiving the communication signal during the communication mode, has a shorter length than the first portion of the coil.

3. The IMD of claim 1, wherein the rectifier is configured to rectify an AC current generated between the first and second terminals of the coil in dependence on the power signal received by the coil from a non-implantable device during the charge or power mode.

4. The IMD of claim 3, further comprising first and second coupling capacitors, and wherein:
   the rectifier includes first and second input terminals, the second input terminal being the input terminal of the rectifier to which the switch is connected, so that the switch is between the second terminal of the coil and the second input terminal of the rectifier; and
   during the charge or power mode, the first coupling capacitor is coupled between the first terminal of the coil and the first input terminal of the rectifier, and the second coupling capacitor is coupled between the second terminal of the coil and the second input terminal of the rectifier.

5. The IMD of claim 1, wherein:
   the communication circuitry is also configured to transmit a communication signal using the coil to a non-implantable device during the communication mode.

6. The IMD of claim 1, further comprising therapy and/or diagnostic circuitry that is powered by a voltage produced using at least one of:
   a rechargeable battery that is charged in dependence on the power signal received by the coil from a non-implanted device, or
   circuitry that converts the power signal received by the coil from a non-implanted device to the voltage.

7. The IMD of claim 6, wherein the therapy and/or diagnostic circuitry includes:
   a pulse generator configured to produce stimulation pulses that are used for cardiac stimulation and/or neurostimulation.

8. The IMD of claim 1, further comprising:
   a diode coupled between the first terminal of the coil and a ground reference;
   wherein the diode sets a DC reference point without sourcing or sinking any current.

9. A method for used by an implantable medical device (IMD) having a coil and a rechargeable battery, wherein the IMD is configured to operate in a charge mode and a communication mode, wherein a first portion of the coil extends between the first and second terminals of the coil, a second portion of the coil extends between the first terminal and the intermediate tar of the coil, and a third portion of the coil extends between the intermediate tap and the second terminal of the coil, and wherein the IMD includes a switch between the second terminal of the coil and an input terminal of a rectifier of power circuitry that is configured to charge the rechargeable battery, the method comprising:
   (a) during the charge mode
      (a1) using the switch to couple the second terminal of the coil to the input terminal of the rectifier and using the first portion of the coil, which may include the entire coil, to receive a power signal from a non-implantable device, and (a2) charging the rechargeable battery of the IMD in dependence on the power signal received using the first portion of the coil;

(b) during the communication mode (b1) using the switch to decouple the second terminal of the coil from the input terminal of the rectifier and using the second portion of the coil, which has a shorter length than the first portion of the coil, to receive a communication signal from a non-implantable device, and (b2) demodulating the communication signal received using the second portion of the coil.

10. The method of claim 9, wherein: step (a) includes coupling the second terminal of the coil to an input terminal of charge circuitry during the charge mode; and step (b) includes decoupling at the second terminal of the coil from the input terminal of the charge circuitry during the communication mode, thereby reducing the using the switch to decouple the second terminal of the coil from the input terminal of the rectifier at step (b.1) reduces an inductance of the coil during the communication mode as compared to an inductance of the coil during the charge mode.

11. The method of claim 9, wherein: step (b) includes preventing the using the switch to decouple the second terminal of the coil from the input terminal of the rectifier at step (b.1) prevents current from flowing through the third portion of the coil, extending between the intermediate tap and the second terminal of the coil, during the communication mode.

12. An implantable medical device (IMD) configured to operate in a charge or power mode and in a communication mode, the IMD comprising:

a coil including a first terminal, a second terminal and an intermediate tap between the first and second terminals;

power circuitry including a rectifier coupled, during the charge or power mode, to a first portion of the coil extending between the first and second terminals of the coil; and communication circuitry coupled to a second portion of the coil extending between the first terminal and the intermediate tap of the coil;

wherein the first portion of the coil, which extends between the first and second terminals of the coil, is used for receiving a power signal during the charge or power mode;

wherein the second portion of the coil, which extends between the first terminal and the intermediate tap of the coil, is used for receiving a communication signal during the communication mode;

further comprising a switch between the second terminal of the coil and an input terminal of the rectifier;

wherein the switch is configured to couple the second terminal of the coil to the input terminal of the rectifier during the charge or power mode;

wherein the switch is configured to decouple the second terminal of the coil from the input terminal of the rectifier during the communication mode, thereby preventing current from flowing through a third portion of the coil, which extends between the intermediate tap and the second terminal of the coil, during the communication mode; and wherein the switch, by decoupling the second terminal of the coil from the input terminal of the rectifier during the communication mode, reduces an inductance of the coil during the communication mode as compared to an inductance of the coil during the charge or power mode.

13. The IMD of claim 12, wherein:

the power circuitry is configured to at least one of charge a rechargeable battery in dependence on a power signal received using the first portion of the coil from a non-implantable device during the charge mode, said battery for use in powering components of the IMD, or generate one or more voltages in dependence on a power signal received using the first portion of the coil from a non-implantable device during the power mode, said one or more voltages for use in powering components of the IMD; and communication circuitry configured to demodulate a communication signal received using the second portion of the coil from a non-implantable device during the communication mode.

14. The IMD of claim 12, further comprising:

a pulse generator configured to produce stimulation pulses that are used for cardiac stimulation and/or neurostimulation;

wherein the pulse generator is powered by a voltage produced using at least one of a rechargeable battery that is charged in dependence on the power signal received by the coil from a non-implanted device, or circuitry that converts the power signal received by the coil from a non-implanted device to the voltage.

* * * * *